United States Patent
Krivitski et al.

(10) Patent No.: US 7,297,280 B2
(45) Date of Patent: *Nov. 20, 2007

(54) METHOD AND APPARATUS TO MEASURE BLOOD FLOW IN HEMODIALYSIS SHUNTS

(75) Inventors: Nikolai M. Krivitski, Ithaca, NY (US); David R. MacGibbon, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 40 days.

This patent is subject to a terminal disclaimer.

(21) Appl. No.: 10/871,319

(22) Filed: Jun. 18, 2004

(65) Prior Publication Data

US 2005/0051496 A1   Mar. 10, 2005

Related U.S. Application Data

(63) Continuation of application No. 10/355,944, filed on Jan. 31, 2003, now Pat. No. 6,926,838, which is a continuation of application No. 09/734,352, filed on Dec. 11, 2000, now Pat. No. 6,514,419, which is a continuation of application No. 09/348,130, filed on Jul. 2, 1999, now Pat. No. 6,210,591, which is a continuation of application No. 09/010,697, filed on Jan. 22, 1998, now Pat. No. 6,153,109, which is a continuation-in-part of application No. 08/965,975, filed on Nov. 7, 1997, now abandoned, which is a continuation of application No. 08/305,953, filed on Sep. 16, 1994, now Pat. No. 5,685,989.

(51) Int. Cl.
*A61B 5/026* (2006.01)
*A61B 5/0275* (2006.01)
*A61B 8/06* (2006.01)

(52) U.S. Cl. .................. 210/739; 210/745; 73/861; 73/861.05; 73/861.07

(58) Field of Classification Search .............. 210/85, 210/87, 90, 97, 646, 739, 745; 604/4.01, 604/5.01; 600/504, 505; 73/861, 861.05, 73/861.07, 861.18

See application file for complete search history.

(56) References Cited

U.S. PATENT DOCUMENTS 3,640,271 A   2/1972   Horton (Continued)

FOREIGN PATENT DOCUMENTS

DE         255 478 A1      4/1988

(Continued)

OTHER PUBLICATIONS

Proc EDTA-ERA (1985) vol. 22, pp. 296-302.*

(Continued)

*Primary Examiner*—John Kim
(74) *Attorney, Agent, or Firm*—Brian B. Shaw; Stephen B. Salai; Harter Secrest & Emery LLP

(57) ABSTRACT

The measurement of blood flow in a dialysis shunt is obtained by injection of an indicator material into a venous line leading from dialysis equipment to the shunt. The blood flow in an arterial line leading from the shunt at a location downstream of the venous line to the dialysis equipment is monitored by an arterial line sensor for the presence of the indicator material. A detector connected to the sensor provides a dilution curve in response to the presence of the indicator material and the blood flow in the shunt is calculated from the area under the dilution curve. The locations of the arterial and venous lines in the shunt can be reversed to obtain a measurement of blood recirculation from the venous line into the arterial line.

20 Claims, 8 Drawing Sheets

U.S. PATENT DOCUMENTS

| | | | |
|---|---|---|---|
| 3,964,479 | A | 6/1976 | Boag et al. |
| 3,990,973 | A | 11/1976 | Boag et al. |
| 4,081,372 | A | 3/1978 | Atkin et al. |
| 4,123,353 | A | 10/1978 | Hakansson et al. |
| 4,136,563 | A | 1/1979 | Mueller et al. |
| 4,153,554 | A | 5/1979 | von der Heide et al. |
| 4,181,610 | A | 1/1980 | Shintani et al. |
| 4,231,366 | A | 11/1980 | Schael |
| 4,353,368 | A | 10/1982 | Slovak et al. |
| 4,391,124 | A | 7/1983 | Drost et al. |
| 4,432,231 | A | 2/1984 | Napp et al. |
| 4,434,648 | A | 3/1984 | Drost et al. |
| 4,508,622 | A | 4/1985 | Polaschegg et al. |
| 4,596,550 | A | 6/1986 | Troutner |
| 4,650,458 | A | 3/1987 | Dahlberg et al. |
| 4,777,958 | A | 10/1988 | Ophir |
| 4,797,655 | A | 1/1989 | Orndal et al. |
| 4,832,484 | A | 5/1989 | Aoyagi et al. |
| 4,856,321 | A | 8/1989 | Smalling et al. |
| 4,897,184 | A | 1/1990 | Shouldice et al. |
| 4,923,598 | A | 5/1990 | Schal |
| 4,938,873 | A | 7/1990 | Rossi |
| 4,966,691 | A | 10/1990 | Brous |
| 4,995,268 | A | 2/1991 | Ash et al. |
| 5,024,756 | A | 6/1991 | Sternby |
| 5,100,554 | A | 3/1992 | Polaschegg |
| 5,230,341 | A | 7/1993 | Polaschegg |
| 5,312,550 | A | 5/1994 | Hester |
| 5,385,143 | A | 1/1995 | Aoyagi |
| 5,510,716 | A | 4/1996 | Buffaloe, IV et al. |
| 5,526,808 | A | 6/1996 | Kaminsky |
| 5,551,422 | A | 9/1996 | Simonsen et al. |
| 5,553,615 | A | 9/1996 | Carim et al. |
| 5,642,734 | A | 7/1997 | Ruben et al. |
| 5,676,143 | A | 10/1997 | Simonsen et al. |
| 5,685,989 | A | 11/1997 | Krivitski et al. |
| 5,690,104 | A | 11/1997 | Kanemoto et al. |
| 5,720,284 | A | 2/1998 | Aoyagi et al. |
| 5,803,908 | A | 9/1998 | Steuer et al. |

FOREIGN PATENT DOCUMENTS

| | | |
|---|---|---|
| EP | 0 018 817 | 11/1980 |
| EP | 0 089 003 | 3/1983 |
| EP | 0 373 455 | 6/1990 |
| SU | 521891 | 7/1976 |
| WO | WO 94/27495 | 12/1994 |
| WO | WO 98/17193 | 4/1998 |

OTHER PUBLICATIONS

C. Aldridge et al., The assessment of arteriovenous fistulae created for haemodialysis from pressure and thermal dilution measurements, Journal of Medical Engineering & Technology, May/Jun. 1984, pp. 118-124, vol. 8, No. 3.

Charles B. Anderson, M.D. et al., Blood flow measurements in arteriovenous dialysis fistulas, Surgery, Apr. 1977, pp. 459-461, vol. 81, No. 4.

David A. Ogden, M.D. et al., In vivo measurement of blood recirculation during "Y" type single needle dialysis, Journal of Dialysis, 1979, pp. 265-176, vol. 3.

Louk F.I.J. Oudenhoven et al., Magnetic resonance, a new method for measuring blood flow in hemodialysis fistulae, Kidney International, 1994, pp. 884-889, vol. 45.

Emil P. Paganini, MD, FACP, Adapting the dialysis unit to increased hematoorit levels American Journal of Kidney Diseases, Apr. 1995, pp. S12-S17, vol. 25, No. 4, Suppl. 1.

James L. Porile et al., Preservation of Vascular Access, Journal of the American Society of Nephrology, 1993, pp. 997-1003, vol. 4, No. 4.

Stanley E. Rittgers, PH.D. et al., Noninvasive blood flow measurement in expanded polytetrafluoroethylene grafts for hemodialysis access, Journal of Vascular Surgery, Apr. 1986, pp. 635-642, vol. 3, No. 4, The C.V. Mosby Company, St. Louis, Mo.

Barry S. Strauch, MD, Forecasting thrombosis of vascular access with doppler color flow imaging, American Journal of Kidney Diseases, Jun. 1992, pp. 554-557, vol. XIX, No. 6.

M. Thomas et al., Measurement of vascular access recirculation without contralateral venous puncture, Nephron, 1992, pp. 224-225, vol. 62.

Zbylut J. Twardowski, MD, All currently used measurements of recirculation in blood accass by chemical methods are flawed due to Intradialytic disequilibrium or recirculation at low flow, American Journal of Kidney Diseases, Dec. 1998, pp. 1046-1058, vol. 32, No. 6.

Zbylut J. Twardowski, Blood recirculation in Intravenous catheters for hemodialysis, Journal of the American Society of Nephrology, 1993, pp. 1978-1981, vol. 3, No. 12.

Jeffrey Sands et al., Access flow measured during hemodialysis, ASAIO Journal, Jan.-Feb. 1996, pp. 841-844, vol. 42, No. 1, Lippencott-Raven Publishers.

ASAIO Journal, Jan.-Feb. 1996, p. 74, vol. 42, No. 1, Lippincott-Raven Publishers.

Journal of the American Society of Nephrology, Sep. 1995, p. 501-502, vol. 6, No. 3.

Journal of the American Society of Nephrology, Sep. 1996, p. 1419, vol. 7, No. 9, Williams & Wilki.

Daniel Schneditz et al., Measurement of access flow during hemodialysis using the constant infusion approach, ASAIO Journal, 1998, pp. 74-81.

Richard A. Sherman, MD et al., Assessment of a two-needle technique for the measurement of recirculation during hemodialysis, American Journal of Kidney Diseases, Jul. 1991, pp. 80-83, Vo.l. XVIII, No. 1.

Richard A. Sherman, MD et al., Rate-related recirculation: The effect of altering blood flow on dialyzer recirculation, American Journal of Kidney Diseases, Feb. 1991, pp. 170-173, vol. XVII No. 2.

Richard A. Sherman, MD et al., Recirculation reassessed: The Impact of blood flow rate and the low-flow method reevaluated, American Journal of Kidney Diseases, Jun. 1994, pp. 846-848, vol. 23, No. 8.

Richard A. Sherman, MD, The measurement of dialysis access recirculation, American Journal of Kidney Diseases, Oct. 1993, pp. 616-621, vol. 22, No. 4.

Mark C. Shu et al., Flow phenomena in compliant and noncompliant arteriovenous grafts, ASAIO Transactions, Jul.-Sep. 1988, pp. 519-523, vol. 34, No. 3.

Robert R. Steuer et al., Enhanced fluid removal guided by blood volume monitoring during chronic hemodialysis, Artificial Organs, 1998, pp. 627-632, vol. 22, No. 8.

Robert R. Steuer et al., Poster Session—Renal 2: Hematocrit as an Indicator of blood volume and a predictor of intradialytic morbid events, ASAIO Journal, Jul.-Sep. 1994, pp. M691-M696, vol. 40, No. 3.

Robert R. Steuer et al., Reducing symptoms during hemodialysis by continuously monitoring the hematocrit, American Journal of Kidney Diseases, Apr. 1996, pp. 525-532, vol. 27, No. 4.

John C. Van Stone, MD et al., Detection of hemodialysis access outlet stenosis by measuring outlet resistance, American Journal of Kidney Diseases, Apr. 1994, pp. 562-568, vol. 23, No. 4.

David W. Windus, MD, Permanent vascular access: A nephrologist's view, American Journal of Kidney Diseases, May 1993, pp. 457-471, vol. 21, No. 5.

Von G. Wittenberg et al., Interobserver-Variabilitat von dialyseshuntflubmessungen unit der farbkodierten duplexsonographie, Fortschr Rontgenstr, 1993, pp. 375-378.

J.A. Barra et al., Interet de la debimetric ultrasonique dans la surveillance post-operatoire et l'evolution des fistules-arterio-veineuses pour l'hemodialyse chronique, Journal d'Urologie et de Nephrologio, 1997, pp. 515-525.

Anatole Besarab et al., Determinants of measured dialysis venous pressure and its relationship to true intra-access venous pressure, ASAIO Transactions, Jul.-Sep. 1991, pp. M270-M271, vol. 37, No. 3.

Anatole Besarab et al., The relationship of recirculation to access blood flow, American Journal of Kidney Diseases, Feb. 1997, pp. 223-229, vol. 29, No. 2.

Journal of the American Society of Nephrology, Sep. 1995, p. 1484, vol. 6, No. 3.

Peter J. Bosman et al., Access flow measurements In hemodialysis patients: In vivo validation of an ultrasound dilution technique, Journal of the American Society of Nephrology, Jun. 1996, pp. 966-969, vol. 7, No. 6.

John D. Bower et al., Circulatory function during chronic hemodialysis, ASAIO, pp. 373-377.

B. Charra et al., A dye-dilution cardiac output technique for hemodialyzed patients with arteriovenous fistula, Kidney International, 1973, pp. 51-53, vol. 3.

A.K. Cheung, Stages of future technological developments in haemodialysis, Nephrol Dial Transplant, 1996, pp. 52-58, vol. 11, Suppl. 8.

Valerie De Precigout et al., Comparison de differentes techniques de surveillance des abords vasculaires chez l'hemodialyse chronique, Nephrologie, 1994, pp. 87-90, vol. 15, No. 2.

Journal of the American Society of Nephrology, Sep. 1995, p. 486, vol. 6, No. 3.

Thomas A. Depner, Nephrology forum—Assessing adequacy of hemodialysis: Urea modeling, Kidney International, 1994, pp. 1522-1535, vol. 45.

ASAIO Journal, Jan.-Feb. 1996, p. 81, vol. 42, No. 1.

Journal of the American Society of Nephrology, Sep. 1996, p. 1407, vol. 7, No. 9.

R.D. Gleed et al., Validation in the sheep of an ultrasound velocity dilution technique for haemodialysis graft flow, Nephrology Dialysis Transplantation, 1997, pp. 1464-1467, vol. 12.

Robert L. Hester, Ph.D. et al., A new technique for determining recirculation in the ESRD Patient, Nephrology News & Issues, Jun. 1993, pp. 44-45.

Robert L. Hester, Ph.D. et al., The determination of hemodialysis blood recirculation using blood urea nitrogen measurements, American Journal of Kidney Diseases, Dec. 1992, pp. 598-602, vol. XX, No. 6.

N.A. Hoenich et al., A technique for the laboratory determination of recirculation in single needle dialysis, The International Journal of Artificial Organs, pp. 63-70, vol. 16, No. 2.

Nicholas Andrew Hoenich et al., Technology and clinical application of large-bore and Implantable catheters, Artificial Organs, pp. 276-282, vol. 18, No. 4.

Jacobo Kelber, MD et al., Factors effecting delivery of high-efficiency dialysis using temporary vascular access, American Journal of Kidney Diseases, Jul. 1993, pp. 24-29, vol. 22, No. 1.

Barry Kirschbaum, MD et al., Study of vascular access blood flow by angiodynography, American Journal of Kidney Diseases, Jan. 1995, pp. 22-25, vol. 25, No. 1.

H.W. Klempt et al., Ergebnisse der farbstoffverdunnungstechnik bei paripheren, arteriovenosen fistein und hyperthyreosen, Eingegangen, Jan. 1975, pp. 863-878, vol. 64.

Nikolai M. Krivitski, Ph.D. et al., Accuracy of dilution techniques for access flow measurement during hemodialysis, American Journal of Kidney Diseases, Mar. 1998, pp. 502-508, vol. 31, No. 3.

Nephrology Dialysis Transplantation, Sep. 1997, p. A129, vol. 12, No. 9.

Journal of the American Society of Nephrology, Sep. 1997, p. 164A, vol. 8.

Journal of the American Society of Nephrology, Sep. 1997, p. 155A, vol. 8.

Journal of the American Society of Nephrology, Sep. 1995, p. 1498, vol. 6, No. 3.

Nikolai M. Krivitski, Novel method to measure access flow during hemodialysis by ultrasound velocity dilution technique, ASAIO Journal, Jul.-Sep. 1995, pp. M741-M744, vol. 41, No. 3.

Journal of the American Society of Nephrology, Sep. 1996, p. 1410, vol. 7, No. 9.

Nikolai M. Krivitski, Theory and validation of access flow measurement by dilution technique during hemodialysis, Kidney International, 1995, pp. 244-250, vol. 48.

ASIAO Journal, Jan.-Feb. 1996, p. 80, vol. 42, No. 1, Lippincott-Raven Publishers.

D. Krpan et al., Measurement of blood flow through AV-fistulae by means of Doppler sonography in regularly haemodialysed patients, 1992, pp. 78-82, vol. 14, No. 2.

Kazuyoshi Kubota et al., Arteriovenous shunt flow measurement by ultrasonic duplex system, ASAIO Transactions, Jul.-Sep. 1987, pp. 144-146, vol. 33, No. 3.

B.M.T. Lantz et al., Determination of blood flow through arteriovenous fistulae and shunts, Acia Radiological Diagnosis, 1979, pp. 727-736, vol. 20.

Robert M. Lindsay et al., A comparison of methods for the measurement of hemodialysis access recirculation, ASAIO Journal, 1998, pp. 191-193.

Journal of the American Society of Nephrology, Sep. 1996, p. 1412, vol. 7, No. 9.

Robert M. Lindsay et al., A device and a method for rapid and accurate measurement of access recirculation during hemodialysis, Kidney International, 1996, pp. 1152-1160, vol. 49.

Robert M. Lindsay, Assessment of access recirculation during haemodialysis, Current Opinion in Nephrology and Hypertension, 1997, pp. 670-674, vol. 6.

Robert M. Lindsay, Hemodialysis access blood flow rates can be measured by a differential conductivity technique and are predictive of access clothing, American Journal of Kidney Diseases, Oct. 1997, pp. 475-482, vol. 30, No. 4.

F. Lopot, Use of continuous blood volume monitoring to detect inadequately high dry weight, The International Journal of Artificial Organs, 1996, pp. 411-414.

Richard E. May, Predictive measures of vascular access thrombosis: A prospective study, Kidney International, 1997, pp. 1656-1662, vol. 52.

D.A. Ogden, Blood recirculation during hemodialysis with a coaxial counterflow single needle blood access catheter, ASAIO Transactions, Apr. 20-21, 1979, pp. 325-327, vol. 25.

Fresenius USA, Inc.'s and Fresenius Medical Care Holdings Inc's Preliminary Invalidity (Aug. 2004).

The use and management of arteriovenous fistulae Fact and fiction Oct. 1991.

Assessment of Arteriovenous Fistulas From Pressure And Recirculation Studies Proc EDTA-ERA(1985) vol. 22.

Vascular Access for Hemodialysis at least as early as Oct. 2004.

The Determination of Hemodialysis Blood Recirculation Using Blood Urea Nitrogen Measurements Dec. 1992.

No. 04-1439 Nonconfidential Reply Brief of Plaintiff-Appellant Transonic Systems, Inc. (Sep. 2004).

First Amended Answer, Affirmative Defenses, Counterclaims, and Jury Demand to Second (Sep. 1999).

NMT's Opening Brief Regarding Claims Construction (Sep. 1999).

Transonic Systems, Inc.'s Reply in Support of Its Motion for Partial Summary Judgment (Jun. 1999).

Opinion and Order (Dec. 1999).

PGC Order Granting NMT's Motion for Summary Judgment of the Issue of Infringement (Aug. 2004).

Memorandum Opinion and Order (Nov. 2000).

Memorandum Opinion & Order (Jun. 2001).

Civil Docket for Case #: 99-CV-41 (Sep. 2004).

Kinetic Modeling in Hemodialysis At least as early as Oct. 2004.

Aldridge C, Greenwood RN, Frampton CF, Wilkinson JS, Cattell WR "Instrument Design for the Bedside Assessment of Arteriovenous Fistulae in Haemodialysis Patients".

Proc EDTNA-ECRA (1985) vol. 14, pp. 255-260, St. Bartholomew's Hospital, London, United Kingdom.

Hester RL, Ashcraft D, Curry E, Bower J "Non-invasive Determination of Recirculation in the Patient On Dialysis" ASAIO Journal 1992, pp. M190-M193.

Greenwood RN, Aldridge C, Goldstein L, Baker LR, Cattell WR Assessment of Arteriovenous Fistulae from Pressure and Thermal Dilution Studies.

Clinical Experience in Forearm Fistulae Clinical Nephrology, vol. 23, No. 4, pp. 189-197.

M. Krämer and HD. Polaschegg, "Automated measurement of recirculation," EDTNA ERCA—Journal XIX No. 2, Apr. 1993, pp. 6-9.

Hans D. Polaschegg, Access Physic, Festschrift for Frank Gotch, (May-Jun. 1999), S-33-S39.

Dr. Thomas Depner, "Techniques for Prospective Detection of Venous Stenosis," Advances in Renal Replacement Therapy, vol. 1, No. 2 (Jul.), 1994; pp. 119-130.

Jan Gothlin, Eric Lindstedt, and Tord Olin, "A Dye-Dilution Method for the Determination of Blood Flow in Cimino-Brescia Arteriovenous Fistulae," 1977, vol. 15, No. 2; pp. 167-168.

Zeitschrift für Kardiologie, Band 62, Heft 2, "The value of oximetry and angiocardiography in detecting left to right intracardiac shunts has been compared", 1972, pp. 158-164.

Paulo Rocha, MD, Jean-Claude Kahn, MD, Gerard Dongradi, MD, Bernard Baron, MD, and Jean-Pierre Fendler, MD, "Arteriovenous Shunt Measured by Bolus Dye Dilution: Reproducibility and Comparison Between Two Injection Sites," Catheterization and Cardiovascular Diagnosis 11:437-481 (1985), pp. 473-481.

David W. Windus, MD, Permanent vascular access: A nephrologist's view. American Journal of Kidney Diseases, May 1993, pp. 457-471, vol. 21, No. 5.

Von G. Wittenberg et al., Interobserver-Variabilität von dialyseshuntflubmassungen unit der farbkodierten duplexsonographie, Fortschr Rontgenstr, 1993, pp. 375-378.

J.A. Barra et al., Interet de la debimetric ultrasonique dans la surveillance post-operetoire et l'evolution des fistules arterio-veineuses pour l'hemodialyse chronique, Journal d'Urologie et de Nephrologlo, 1997, pp. 818-825.

Valerie De Precigout et al., Comparaison de differentes techniques de surveillance des abords vasculaires chez l'hemodialyse chronique, Nephrologie, 1994, pp. 87-90, vol. 15, No. 2.

Nicholas Andrew Hoenich et al., Technology and clinical application of large-bore and Implantable catheters, Artificial Organs, pp. 276-282, vol. 18, No. 4 (1994).

Jacobo Kelber, MD et al., Factors affecting delivery of high-efficiency dialysis using temporary vascular access, American Journal of Kidney Diseases, Jul. 1993, pp. 24-29, vol. 22, No. 1.

Barry Kirschbaum, MD et al., Study of vascular access blood flow by anglodynography, American Journal of Kidney Diseases, Jan. 1995, pp. 22-25, vol. 25, No. 1.

H.W. Klempt et al., Ergebniase der farbstoffverdunnungstechnik bei paeripheren, arteriovenosen fistein und hyperthyreosen, Eingegangen, Jan. 1975, pp. 863-876, vol. 64.

* cited by examiner

METHOD AND APPARATUS TO MEASURE BLOOD FLOW IN HEMODIALYSIS SHUNTS

CROSS-REFERENCE TO RELATED APPLICATIONS

The present application is a continuation of U.S. Ser. No. 10/355,944 filed Jan. 31, 2003, now U.S. Pat. No. 6,926,838, which is a continuation of U.S. Ser. No. 09/734,352 filed Dec. 11, 2000, now U.S. Pat. No. 6,514,419 issuing Feb. 4, 2003, which is a continuation of U.S. Ser. No. 09/348,130 filed Jul. 2, 1999, now U.S. Pat. No. 6,210,591 issuing Apr. 3, 2001, which is a continuation of U.S. Ser. No. 09/010,697 filed Jan. 22, 1998, now U.S. Pat. No. 6,153,109 issuing Nov. 28, 2000, which is a continuation-in-part of U.S. Ser. No. 08/965,975 filed Nov. 7, 1997, now abandoned, which is a continuation of U.S. Ser. No. 08/305,953 filed Sep. 16, 1994, now U.S. Pat. No. 5,685,989 issuing Nov. 11, 1997, each of which is expressly incorporated by reference.

STATEMENT REGARDING FEDERALLY SPONSORED RESEARCH OR DEVELOPMENT

Not Applicable.

BACKGROUND OF THE INVENTION

Field of the Invention

The invention relates to the field of kidney dialysis processes and more particularly to such processes for measuring arterio-venous shunt blood flow and undesirable recirculation during hemodialysis.

Dialysis is a process by which an artificial kidney replaces the function of a patient's kidney. Blood is removed from the patient's vascular system via an arterial line, is passed through a dialyzer and is returned to the patient via a venous line for normal circulation through the patient's vascular system. A majority of dialysis patients have an arteriovenous shunt implanted in a location having a high blood flow that simplifies the withdrawal of blood from the part that is closer to the arterial side of the shunt and the return of purified blood downstream of the withdrawal site, closer to venous side of the shunt. In some cases the shunt clots or stenoses and the resulting reduction in blood flow necessitates surgery that is costly and invasive for the patient. In the situation of low blood flow in the shunt or, if there is any other problem with the venous outflow, some part of the freshly dialyzed blood from the venous return line flows directly to the arterial withdrawal line where it is again filtered. If this undesired direct recirculation level is high enough, some amount of blood will be repeatedly refiltered and the rest of the patient's blood will not be sufficiently filtered to provide the patient with adequate dialysis.

One method of measuring shunt blood flow currently uses color coded duplex sonography. This is very expensive and involves operation by highly-qualified professionals. Measurements are therefore made only rarely and the onset of reduced flow, when treatment could be made without surgery can be missed.

The standard test for undesired direct recirculation requires three blood samples while the patient is on dialysis. This method requires blood samples from the patient, time from the nurses, and high laboratory costs. Dialysis patients generally have lower hematocrit than the normal population and are at greater risk from losing blood, so this is not very satisfactory.

Another technique involves injection of a saline solution intravenously and recording changes of blood optical properties for detecting recirculation qualitatively. This technique leaves open the question of whether recirculation is quantitatively reduced sufficiently to warrant intervention.

BRIEF SUMMARY OF THE INVENTION

The present invention avoids the problems encountered with previous methods and techniques by providing an accurate determination of shunt blood flow and undesired recirculation at lower cost.

Blood flow, Q, measured by the dilution method (A. C. Guyton Textbook of Medical Physiology, Sixth Edition, p. 287, 1981) is given by:

$$Q = V/S \tag{Eq. 1}$$

where V is the amount of injected indicator and S is the area under a dilution curve and is equal to the average concentration of indicator in the blood for the duration of the curve, multiplied by the duration of the curve.

A dilution curve is obtained by measuring changes in a physical parameter of the blood over a period of time, and plotting the resulting variations. For example, if the blood parameter being measured is sound velocity, the injection of an indicator such as a saline solution, having a different sound velocity than blood, will produce a change in the measured parameter as the indicator passes the sensor location. The indicator dilutes the blood, and produces a sound velocity curve which is a measure of that dilution. Although injection of a saline solution is convenient for producing a measurable change in a blood parameter such as sound velocity, other changes of parameters may also be suitable. Thus, changes in temperature, electrical impedance, optical characteristics, and the like may also be used as indicators to produce dilution curves. For purposes of this disclosure, however, reference will primarily be made to the use of saline solution as the indicator, with resulting changes in sound velocity in the blood being measured to provide a dilution curve.

To facilitate the measurement of shunt blood flow in accordance with the present invention, the blood line connection is reversed from normal; that is, the arterial inlet which removes the blood from the patient for dialysis is located downstream (not upstream as normal) of the venous outlet in the shunt. A volume of indicator, such as a saline solution, is injected into the venous line ($V_{ven}$), where it is mixed with the dialyzer blood flow $Q_{dial}$ and the mixture is delivered to the shunt where it is combined with the blood flow in the shunt ($Q_{shunt}$). The blood shunt flow ($Q_{shunt}$) can be calculated from Equation 1 by measuring the dilution area in the arterial line $S_{art}$:

$$Q_{shunt} + Q_{dial} = V_{ven}/S_{art} \tag{Eq 2}$$

or $$Q_{shunt} = V_{ven}/S_{art} - Q_{dial} \tag{Eq. 3}$$

Equation 3 shows that if the blood flow through the dialyzer $Q_{dial}$ is measured and the absolute concentration of indicator in the arterial blood line $S_{art}$ is recorded, then the blood flow through the shunt $Q_{shunt}$ can be calculated.

In some methods applicable to hemodialysis, sensors are clamped onto the exterior of the arterial or venous line, or tube. However, it is difficult to measure the absolute concentration of indicator in the blood through the hemodialysis tube. For example, if a sound velocity sensor is used to record protein concentration changes in blood due to a saline indicator injection, the sound beam will have to pass through both the tube and the blood. Recorded measurements of absolute sound velocity will be influenced not only by the blood, but also by the unknown sound properties of the tube. The same problem occurs if an optical sensor is clamped onto tube; i.e., the recorded amplitude of a light beam is not only the function of hemoglobin concentration but of tube properties.

This problem may be solved by an additional calibration injection of the same indicator, which is injected in the arterial line, but upstream of the place where the measurements are made. The equation for this case will be:

$$Q_{dial} = V_{cal}/S_{cal} \qquad \text{(Eq. 4)}$$

where $V_{cal}$ is the known quantity of indicator in the calibration injection and $S_{cal}$ is the area under the resulting dilution curve. This area is the average concentration of indicator in the blood for the duration of the curve, times the duration of the curve.

From Equations 2 and 4 the formula for shunt blood flow will be:

$$Q_{shunt} = Q_{dial}(V_{ven}/V_{cal} * S_{cal}/S_{art} - 1) \qquad \text{(Eq. 5) or}$$

$$Q_{shunt} = (V_{ven}/S_{art} - V_{cal}/S_{cal}) \qquad \text{(Eq. 6)}$$

Equation 5 is suitable if blood flow in the tube can be measured accurately. The ratio $S_{cal}/S_{art}$ shows that the recorded dilution areas only need to be proportional to relative changes in concentrations in this case. Assuming that tube properties are constant during the measurements, the value of this ratio can be calculated with high accuracy for most type of sensors, including sound velocity, optical, etc.

Equation 6 can be used where tube blood flow is unknown but absolute concentrations are measured, for instance by withdrawing the blood from the arterial blood line and using an optical densitometer for optical dye dilution measurements.

To avoid the need for a calibration injection, an additional sensor that is matched to the arterial line sensor is located on the venous line downstream of the location of the intravenous indicator injection. For this case, the injected indicator will be mixed with the venous line tube flow, so by analogy with the calibration injection of Equation 4:

$$Q_{dial} = V_{ven}/S_{ven} \qquad \text{(Eq. 7)}$$

where $S_{ven}$ is the area under the dilution curve and is calculated as the average concentration of indicator in the blood for the duration of curve, times the duration of the curve. From the same injection, the area $S_{art}$ is generated. The formula for blood flow by substituting in Equation 5 is:

$$Q_{shunt} = Q_{dial}(S_{ven}/S_{art} - 1) \qquad \text{(Eq. 8)}$$

As an alternative to the foregoing, a measurement of the quantity of blood recirculation may be made during a normal connection of the dialysis blood lines of the shunt, with the intake to the arterial line being upstream in the shunt and the outlet of the venous line connection being downstream in the shunt. With this "normal" connection, after injecting an indicator into the venous line, a rapid appearance of indicator in the arterial line is an indication that recirculation exists. The quantity of recirculation is the fraction of freshly filtered blood in the venous line that recirculates to the arterial line and this quantity is equal to the ratio of indicator volume that is recirculated into the arterial line ($V_{rec}$) to the volume that was injected into the venous line ($V_{ven}$).

The amount of recirculated indicator $V_{rec}$ is equal to the area under the recirculated concentration dilution curve $S_{rec}$ multiplied by the dialysis blood flow in the arterial line $Q_{dial}$:

$$V_{rec} = S_{rec} * Q_{dial} \qquad \text{(Eq. 9)}$$

The same problem with the evaluation of $S_{rec}$ that was described for Equations 2 and 3 persists; namely, the difficulty of measuring indicator concentration through the tubing. This problem is avoided by an additional calibration injection of the same indicator into the arterial line upstream from the place where the measurements are made, as discussed above with respect to Equation 4. From Equations 4 and 9 the recirculating fraction is:

$$V_{rec}/V_{ven} = V_{cal}/V_{ven} * S_{rec}/S_{cal} \qquad \text{(eq. 10)}$$

The ratio $S_{rec}/S_{cal}$ in Equation 10 indicates that the measured dilution areas need only be in the same relative units. Assuming that tube properties are constant during the measurements, this ratio can be calculated with high accuracy for most types of sensors; e.g., sound velocity, optical, etc.

To avoid the need for a calibration injection, an additional sensor that is matched to the arterial line sensor may be located on the venous line downstream of the location of the intravenous indicator injection. For this case, the injected indicator will be mixed with the venous line flow, so by analogy with the calibration injection Equation 7:

$$V_{rec}/V_{ven} = S_{rec}/S_{ven} \qquad \text{(Eq. 11)}$$

In summary, the, shunt blood flow can be measured by reversing arterial and venous blood lines. An arterial inlet, which removes blood from a patient's vascular system, is located in the shunt downstream of a venous outlet, which returns treated blood to the patient's vascular system. An indicator material is injected into an injection port in the venous tube, and changes in the physical properties of the blood are monitored in the arterial line. These changes are recorded, with the area under the resulting dilution curve providing a measure of blood flow in the shunt and tube line. The indicator used for this purpose is any material or blood treatment which changes the physical characteristics of the blood. For example, it can be a saline solution, preferably of known concentration, or can be a heating or cooling of a quantity of blood. The change of characteristics is measured by known sensors, such as sound velocity sensors, electrical impedance sensors, optical sensors, thermal sensors, isotope sensors, or the like, and the blood flow relationships are calculated in accordance with the foregoing equations.

Because the tubing used to carry blood from the patient to the dialysis equipment introduces errors into the measurements of blood flow, calibration measurements may be required, using a calibration injection and, if blood flow is unknown, blood concentration measurements. To avoid the need for a calibration injection, an additional sensor may be provided on the venous line downstream of the venous injection port.

Blood recirculation can also be measured with the arterial inlet located in the shunt upstream of the venous outlet. In this case, the indicator is injected into an injection port in the venous line outlet (as before) and the blood characteristics are monitored in the arterial line. A calibration injection may be provided at an injection port in the arterial line upstream of the arterial tube monitor or, to avoid a calibration injection, a second blood characteristic monitor can be provided in the venous tube downstream of the venous injection port.

BRIEF DESCRIPTION OF THE SEVERAL
VIEWS OF THE DRAWING(S)

The foregoing, and additional objects, features, and advantages of the present invention will become apparent to those of skill in the art from the following detailed description of preferred embodiments thereof, taken in conjunction with the accompanying drawings, in which.

Figure 6:
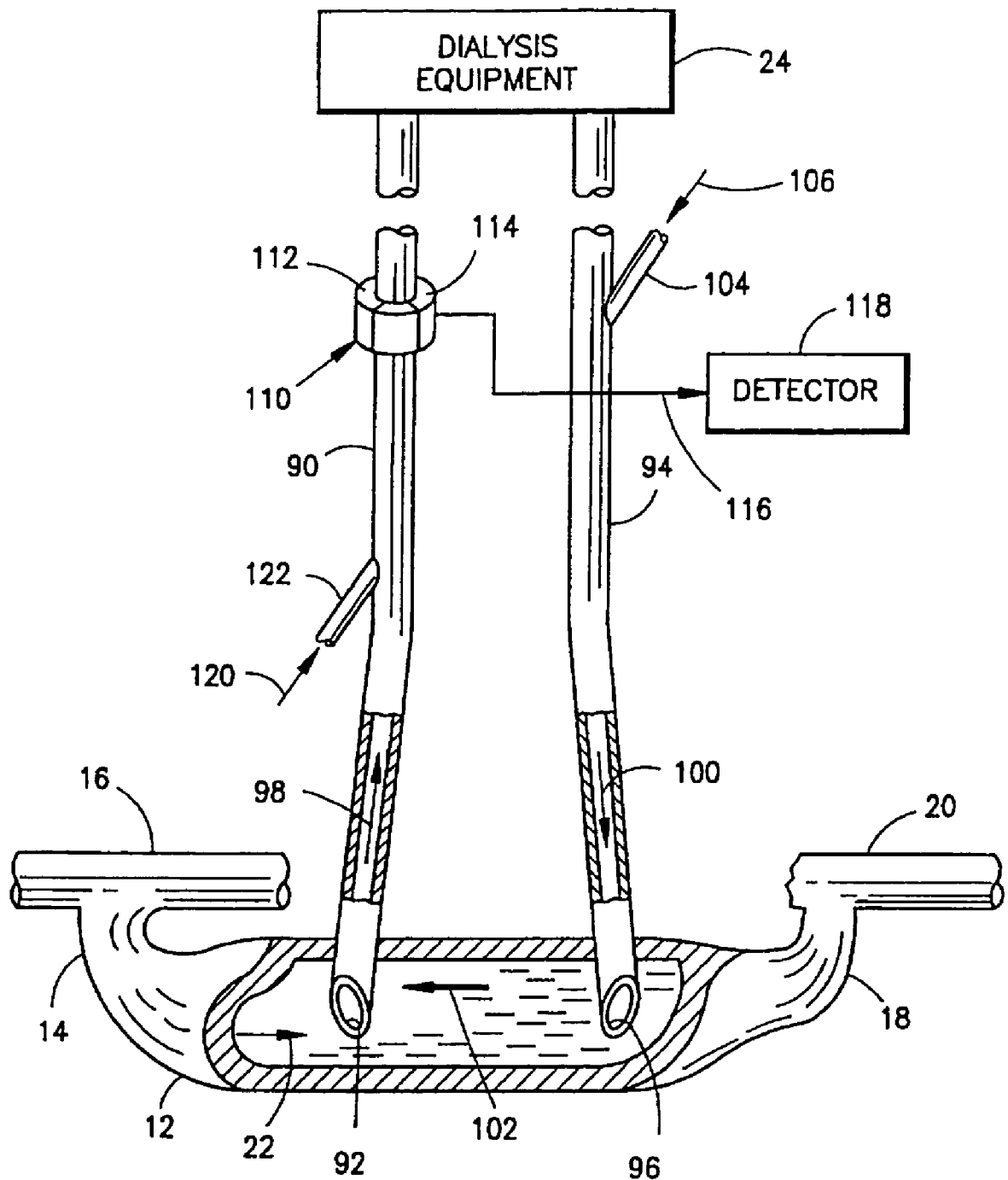
Figure 7:
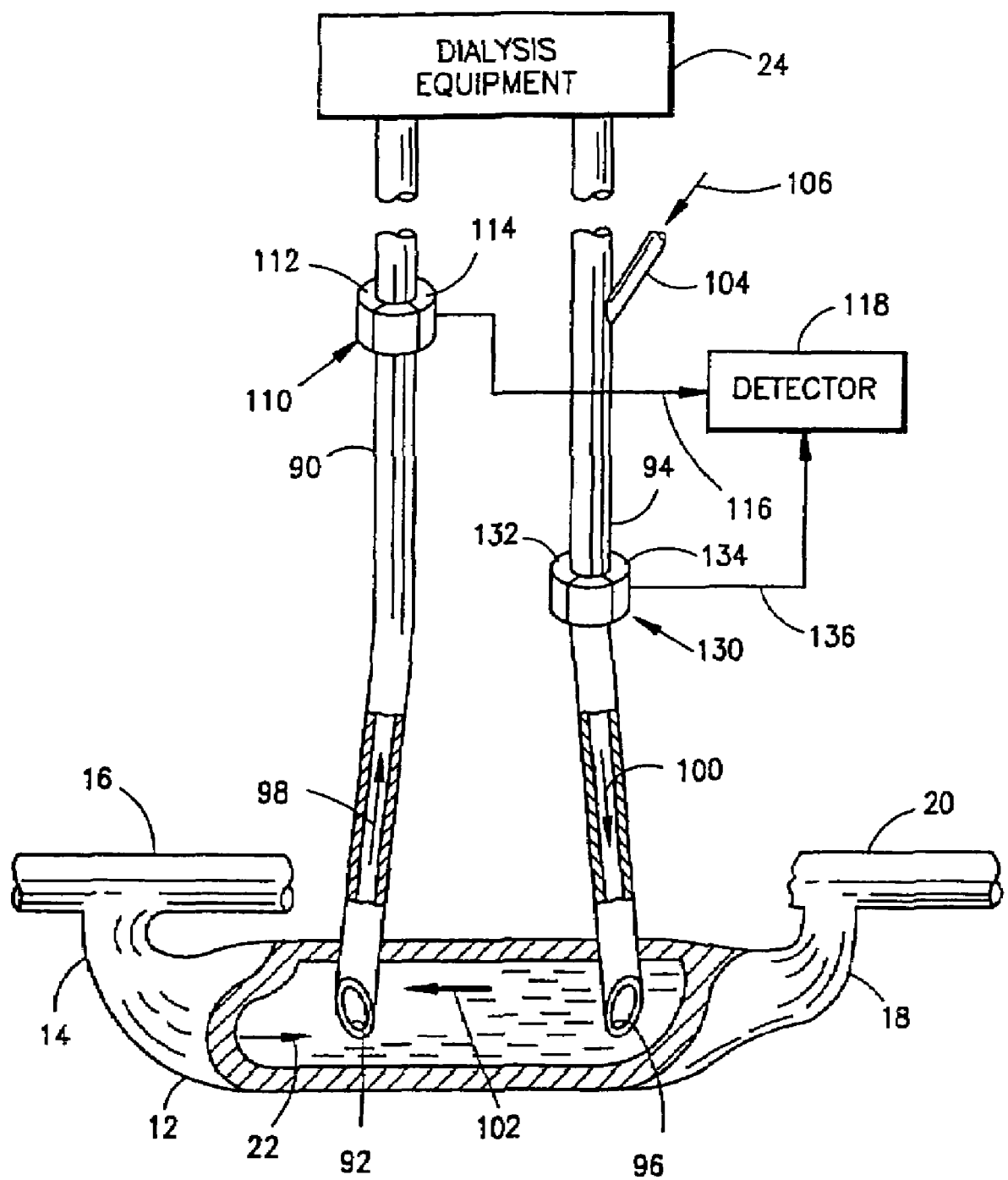

FIG. 6 is a diagrammatic illustration of a second embodiment of the invention, illustrating an arterio-venous shunt connected by way of arterial and venous tubes to a dialyzer, with an arterial tube inlet in the shunt upstream of a venous tube outlet, an injection port in the venous tube, a sensor for the arterial tube and a calibration port in the arterial tube upstream of the sensor; and FIG. 7 is a diagrammatic illustration of a modification of the device of FIG. 6, wherein the calibration port of FIG. 6 is replaced by a venous tube sensor downstream of the venous tube injection port.

DETAILED DESCRIPTION OF THE INVENTION

Figure 1:
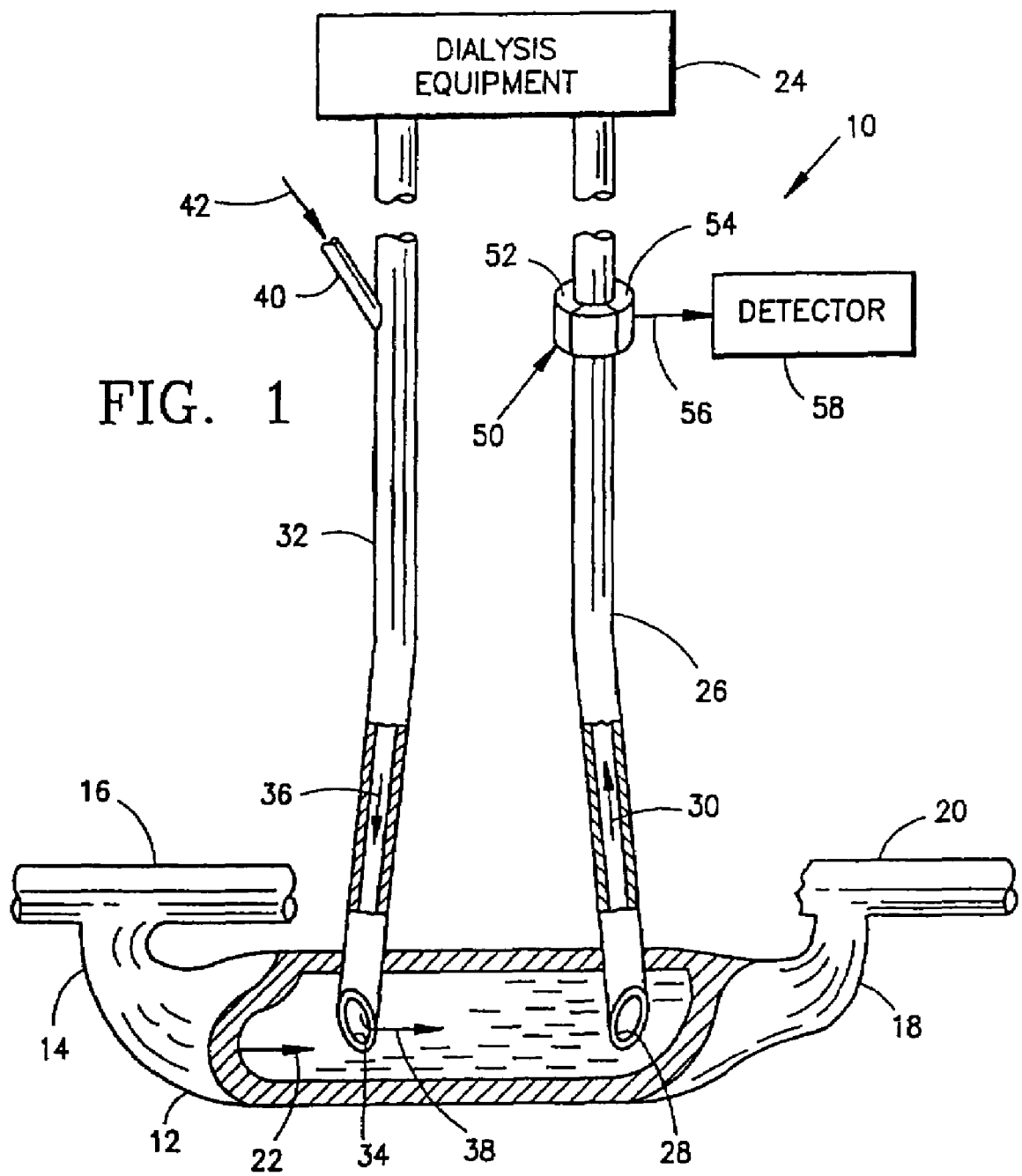
FIG. 1 is a diagrammatic illustration of an arterio-venous shunt connected by way of arterial and venous tubes to a dialyzer with an arterial tube inlet in the shunt downstream from a venous tube outlet, an injection port in the venous tube, and a sensor for the arterial tube.

Turning now to a more detailed consideration of the process of determining blood flow in a dialysis shunt in accordance with the present invention there is illustrated in FIG. 1 a patient blood dialysis system 10 utilizing a reversed connection of arterial and venous lines to a blood vessel 12 illustrated as an arterio-venous shunt connected at its upstream end 14 to a patient's artery 16 and connected at its downstream end 18 to a patient's blood vein 20. The shunt may be an artificial vessel or a native vessel that is surgically moved between artery 16 and vein 20. The direction of flow of blood in the vessel 12 is indicated by arrow 22 and it is this blood flow which is to be determined. Connected between vessel 12 and conventional blood dialysis equipment 24 is an arterial line, or tube 26 having an inlet 28 in the shunt 12 for drawing blood for treatment by the dialysis equipment. The direction of flow of blood in arterial line 26 is illustrated by arrow 30.

Also connected between the dialysis equipment 24 and shunt 12 is a venous line, or tube, 32 which carries treated blood from the dialysis equipment 24 back to the shunt. The venous line 32 has an outlet 34 located in shunt 12, upstream of the arterial line inlet 28. The direction of flow of treated blood in venous line 32 is illustrated by arrow 36. As illustrated by arrow 38, treated blood from the outlet 34 travels downstream, in the direction of the main flow 22, toward the inlet 28 where some of the treated blood 38 is collected by the arterial line 26.

Measurement of blood flow in the shunt is obtained, in accordance with the invention, by injecting into venous line 32, as by way of an injection port 40, an indicator material having a selected physical property differing from that of the blood being treated. In the preferred embodiment, this material, indicated by arrow 42, is a saline solution which is isotonic with the blood but which has different sound velocity properties. Other indicator materials may be, for example, heated or cooled blood. The injected indicator is mixed with the blood flow 36 in the venous line and is returned to shunt 12 where it is mixed with the shunt flow 22. A portion of the indicator is withdrawn from the shunt by the arterial blood line, as indicated by arrow 30.

A sensor 50 is provided at a location downstream of the injection port 40, and preferably is located in the arterial line 26, as illustrated in FIG. 1. The sensor preferably is a blood sound velocity detector which comprises a sound source 52 sending a sound beam directly through the blood passing through arterial line 26 to a sound receiver 54 which produces an output signal related to the velocity of sound in the blood. Such sound velocity sensors are well known in the art and are exemplified by the Transonic 4x perivascular probe manufactured by Transonic Systems, Inc., Ithaca, N.Y., U.S.A. In this probe, the receiver 54 produces an output signal on line 56 which is directed to a detector 58 which measures and evaluates the signal supplied by way of line 56. The detector records the signal and carries out the calculations described above for converting the sensor output signal to a blood concentration signal for determination of the blood flow in the shunt 12 and through the dialysis equipment 24. If the blood flow in the dialysis equipment 24 is significant in comparison to the flow in shunt 12, the measurements made by sensor 50 will give results which over state the flow of the shunt.

Figure 1A:
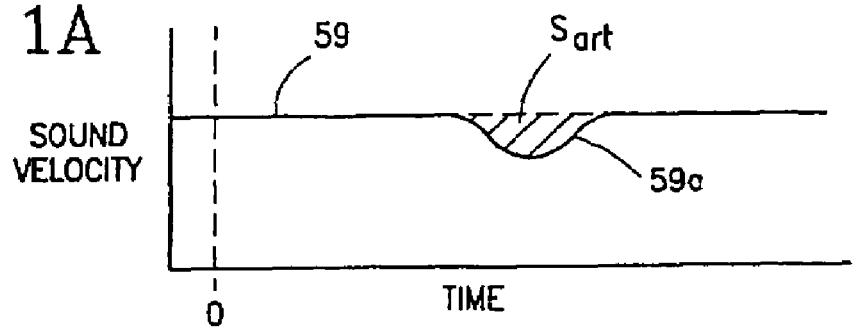
FIG. 1A illustrates a dilution curve for the device of FIG. 1.

More particularly, the blood flow Q in shunt 12 may be calculated in accordance with Equation 1 by calculating the area under the dilution curve obtained by sensor 50. An example of such a curve is illustrated in FIG. 1A, wherein the velocity of sound in the arterial blood flow is illustrated by curve 59. At time 0 an indicator material is injected at port 40, and at some later time, the change in sound velocity caused by the indicator is detected at sensor 50, as illustrated by the dip, or dilution area, 59a in curve 59. The area under the dilution curve 59 in region 59a is the area $S_{art}$ described in Equation 2.

Figure 2:
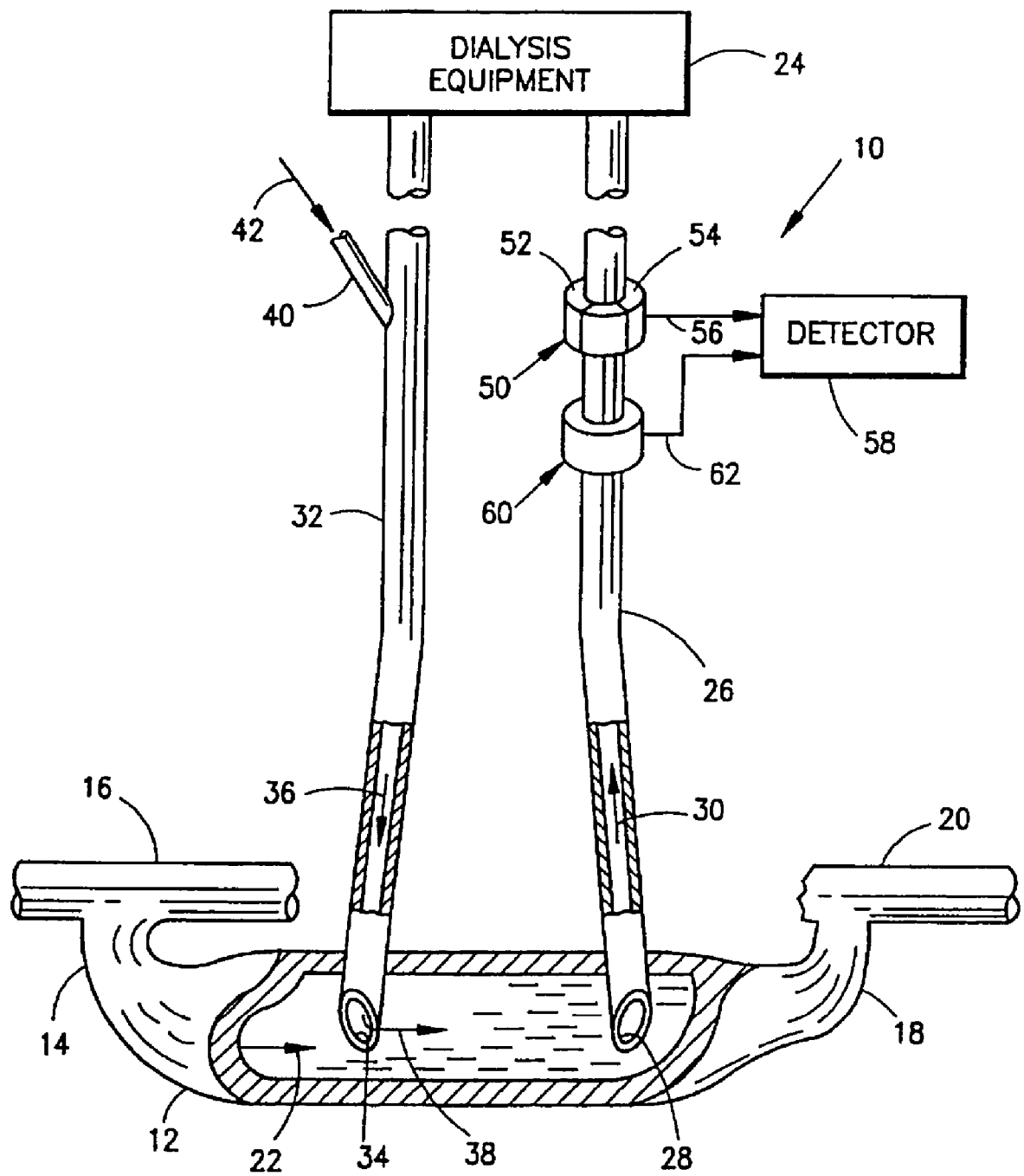
FIG. 2 is a modification of FIG. 1, adding a second sensor for the arterial tube.

As illustrated in FIG. 2, a second blood flow sensor 60 may be provided on arterial line 26 and connected by way of line 62 to the detector 58. This second sensor is a blood flow sensor such as a model HT109 clamp-on flowmeter produced by Transonic Systems, Inc., and is used to measure the blood flow $Q_{dial}$ in line 26 so that it can be subtracted from the sum of flows calculated in accordance with the embodiment of in FIG. 1 to increase the accuracy of the shunt blood flow determination. This improved accuracy is obtained in accordance with Equations 2 and 3. Although sensor 60 is shown as separate from sensor 50, the two sensors may be incorporated into a single unit, if desired.

Figure 3:
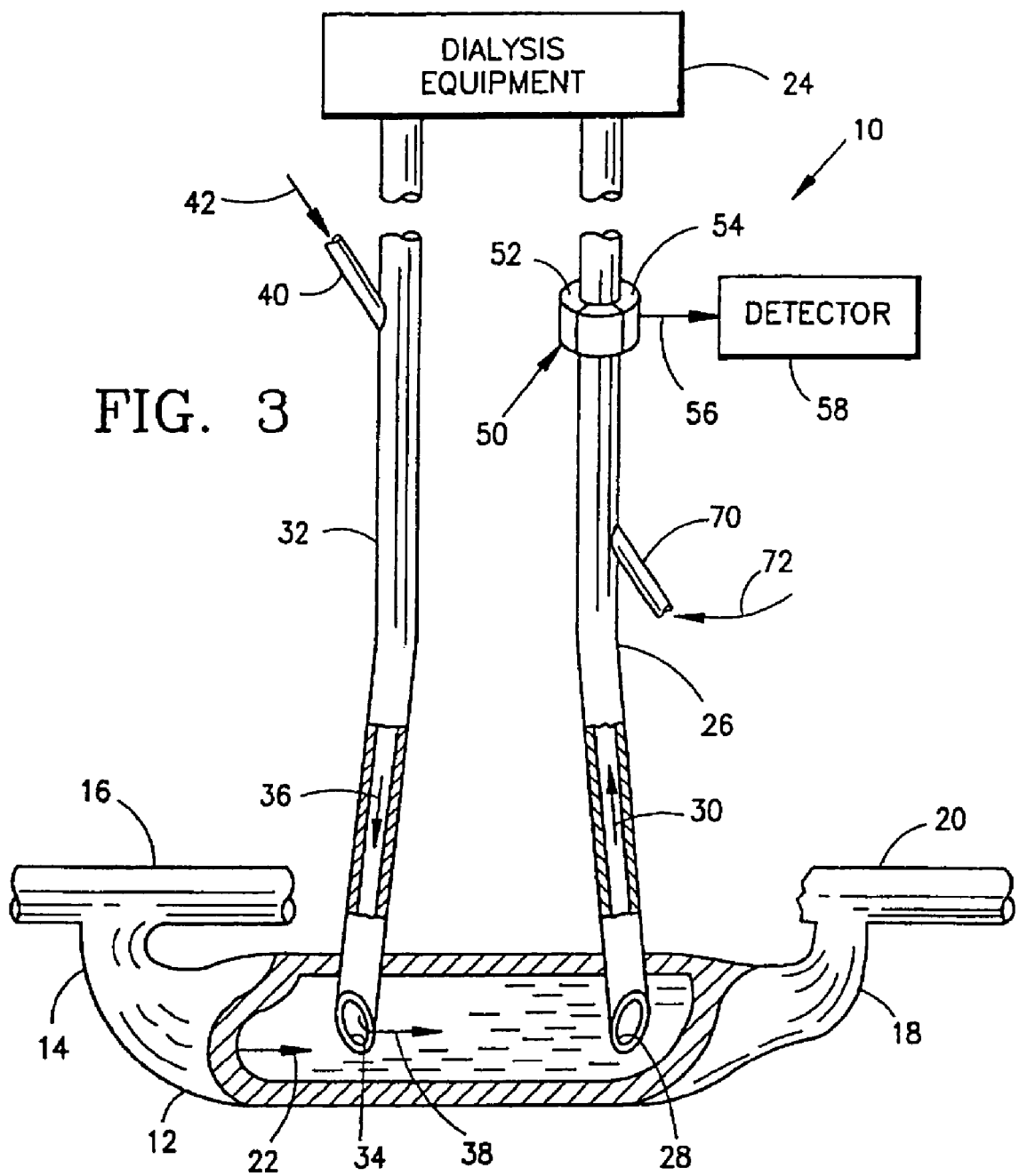
FIG. 3 is a second modification of FIG. 1, adding an injection port in the arterial tube, upstream of the arterial sensor.
Figure 3A:
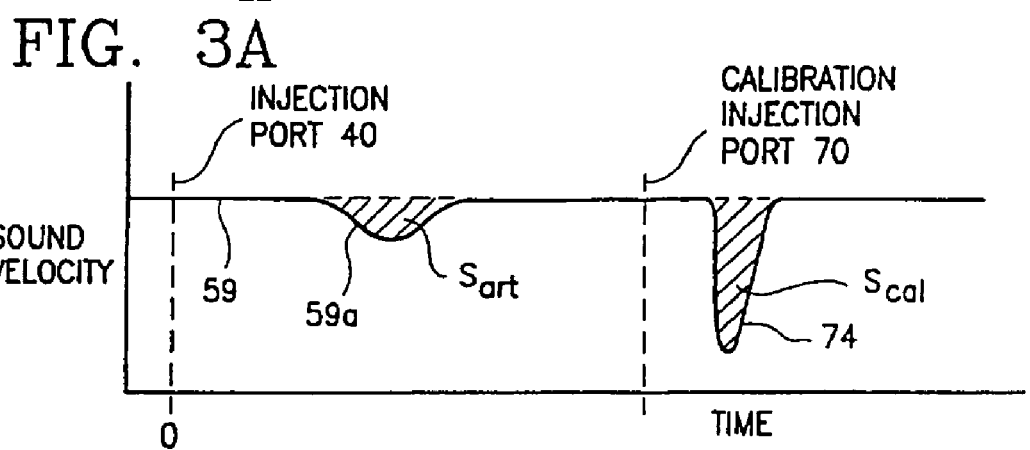
FIG. 3A illustrates a dilution curve for the device of FIG. 3.

Another modification of the invention is illustrated in FIG. 3, which is the same as FIG. 1 but with the addition of an injection port 70 in the arterial line 26 for injecting a calibration indicator material, shown by line 72. This injection port 70 is located upstream of the sensor 50 so that the indicator material 72 is mixed with all of the blood flow in line 26. The injection of the calibration indicator material in port 70 produces a corresponding dilution curve illustrated at 74 in FIG. 3A in accordance with the change in sound velocity in the blood, as sensed by sensor 50, and this dilution curve is recorded by detector 58. The detector determines the blood flow $Q_{dial}$ in line 26 from the area $S_{cal}$ under curve 74 and from the known volume $V_{cal}$ of indicator material 72, in accordance with equation 4. This blood flow $Q_{dail}$ is then subtracted from the sum of flows calculated in accordance with FIG. 1 to increase the accuracy of the shunt blood flow measurement, in accordance with Equation 6.

Figure 4:
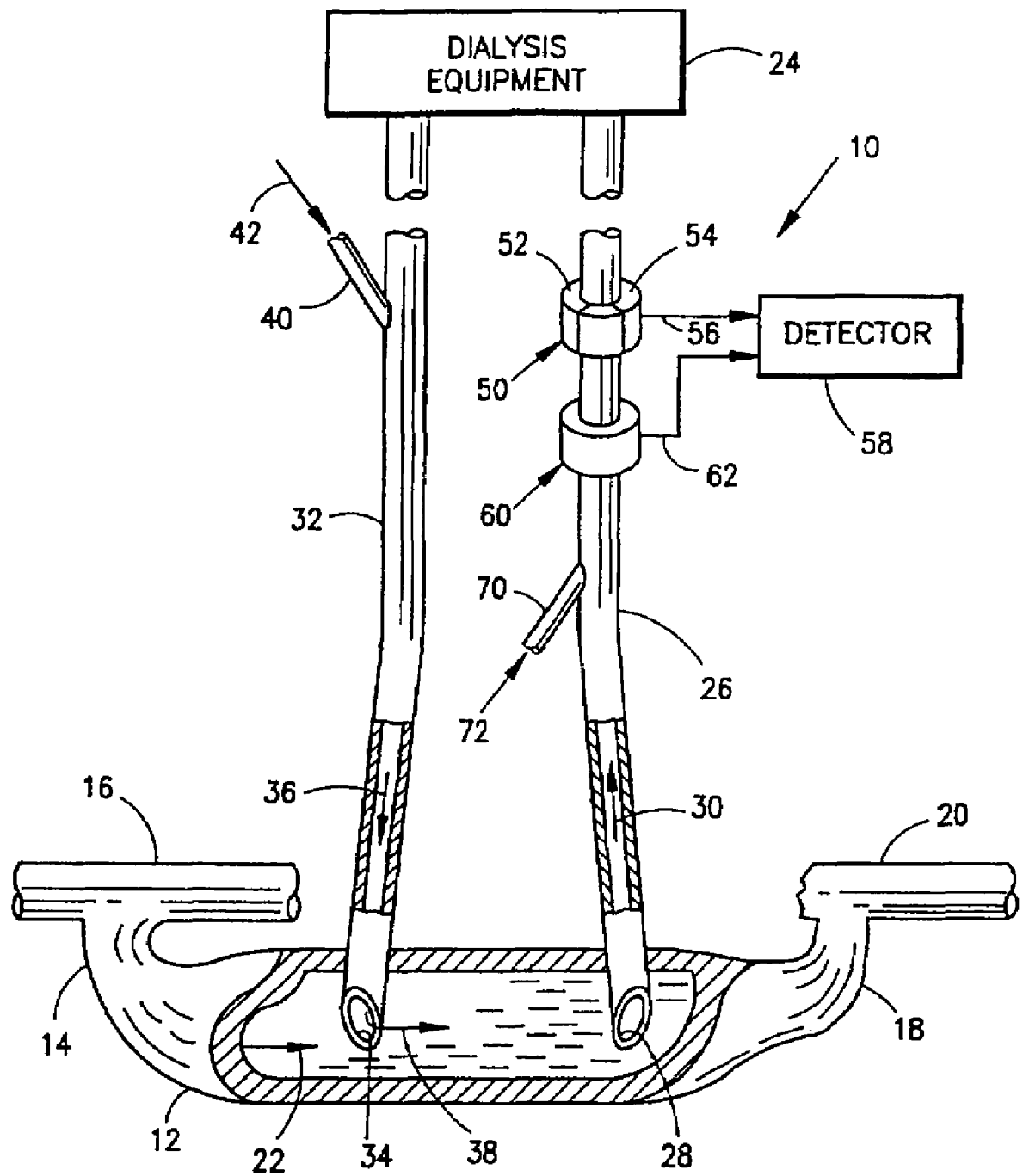
FIG. 4 is a third modification of FIG. 1, adding to the device of FIG. 3 a second arterial sensor of the type illustrated in FIG. 2.

Another embodiment of the invention is illustrated in FIG. 4, which includes all of the measurements of FIGS. 1, 2, and 3. Thus, the device of FIG. 4 includes sensor 50 with a sound source 52 and a sound receiver 54 supplying signals on line 56 to detector 58, includes a blood flow sensor 60 connected by way of line 62 to detector 58, and includes a calibration injection port 70 for receiving calibration indicator material 72. The output signal on line 62 is for measuring the dialysis blood flow $Q_{dial}$. The indicator 72 is a calibration injection, as described above, and relative changes of sound velocity related to known blood flow $Q_{dial}$ are measured by sensor 50. The relative changes of sound velocity corresponding to injections made into port 40 of indicator material 42 and into port 70 of the same indicator material 72 are recorded by sensor 50, so that relative changes of sound velocity in arterial line 26 due to these injections can be calculated in detector 58 to obtain an accurate shunt blood flow measurement in accordance with equation 5.

Figure 5:
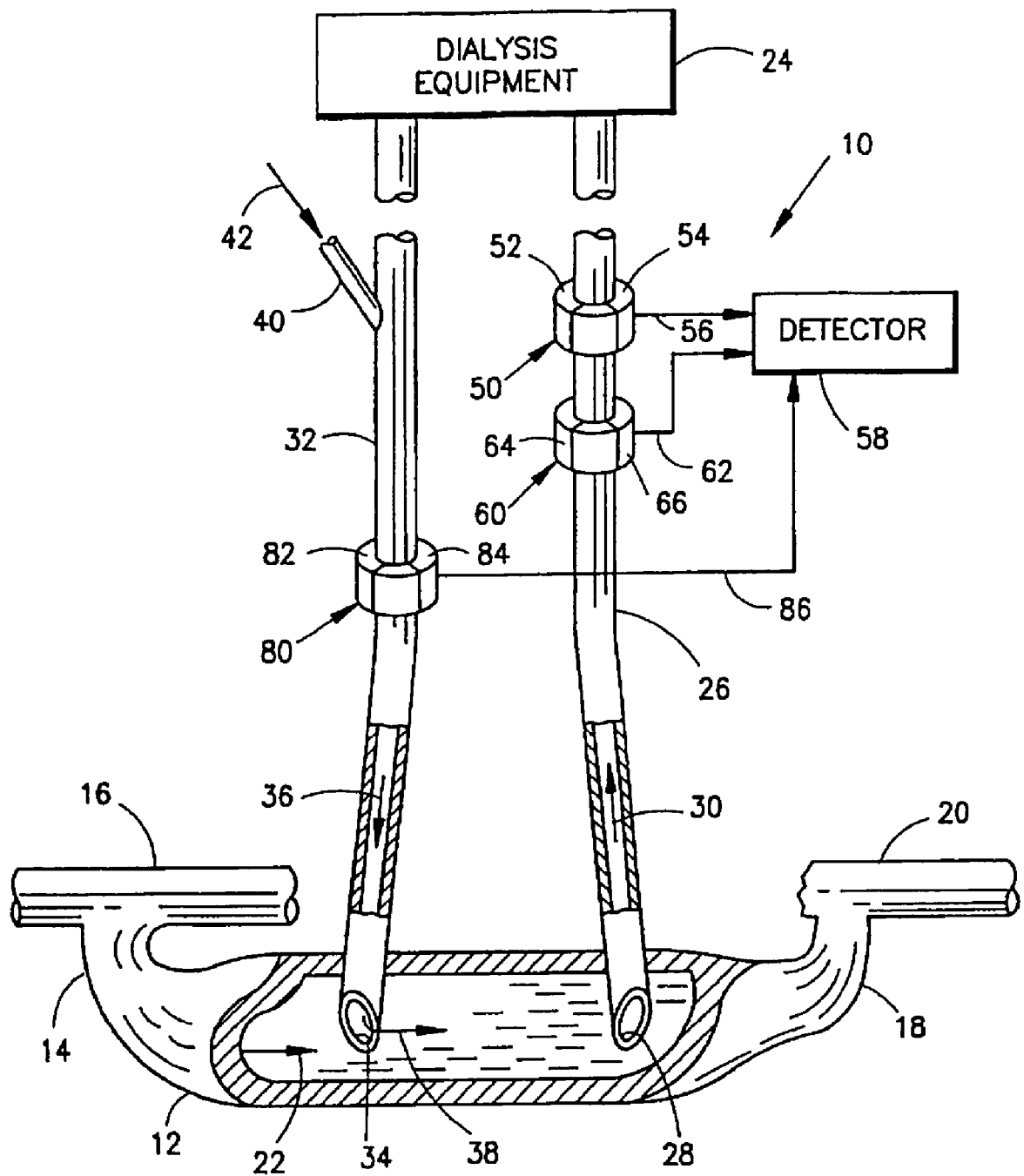
FIG. 5 is a fourth modification of FIG. 1, incorporating two additional sensors, one for each of the venous and arterial tubes.
Figure 5A:
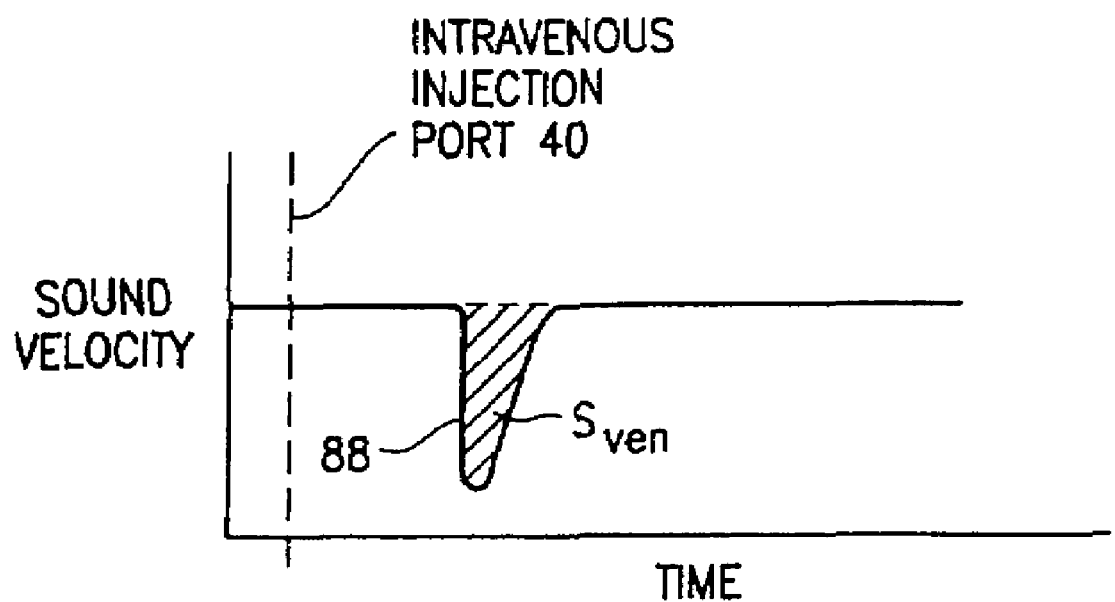
FIGS. 5A and 5B illustrate dilution curves for the device of FIG. 5.
Figure 5B:
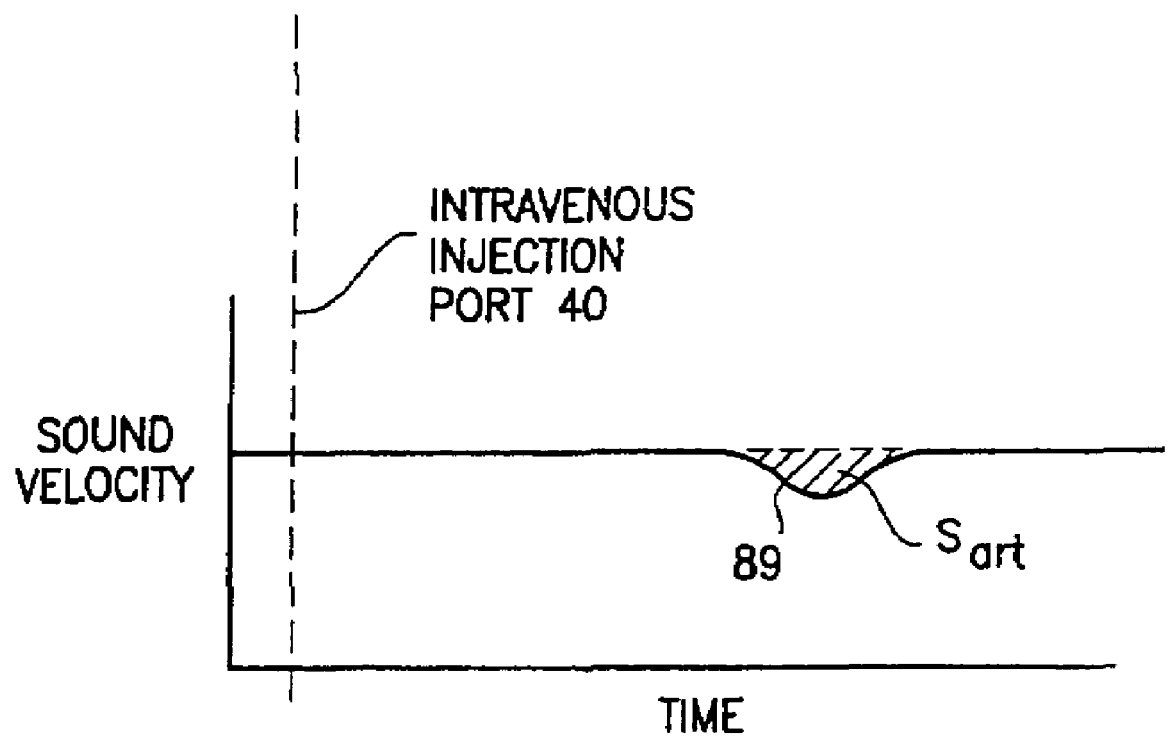

Still another embodiment of the invention is illustrated in FIG. 5, which is similar to the embodiment of FIG. 2 but with the addition of a sensor 80 located on the venous line, or tube, 32. Sensor 80 includes a sound transmitter 82 and a sound receiver 84, the receiver producing an output signal on output line 86 which is connected to detector 58. The use of sensor 80 avoids the need for additional calibration injections in arterial line 26. The additional sound velocity source 82 and receiver 84 match the sound velocity source 52 and receiver 54, and sensor 80 is located downstream of the injection port 40 in venous line 32. As a result, all of the indicator material 42 flows through sensor 80, producing dilution curve 88 (FIG. 5A). The injection made in port 40 is mixed only with the blood flow in venous line 32, and thus serves to calibrate the sensor 80. The same injection later generates dilution curve 89 in the matching sensor 50 (FIG. 5B) after the indicator material passes through the shunt vessel 12, and a portion is recirculated into arterial line 26. The calculation of shunt blood flow $Q_{shunt}$ is then made in accordance with Equation 8.

A second embodiment of the invention is illustrated in FIG. 6, to which reference is now made. This embodiment provides a measurement of undesired recirculation of freshly purified blood while utilizing a "normal" connection of the dialysis equipment lines. Thus, in this embodiment the dialysis equipment 24 is connected to a patient's vascular system by way of shunt 12 and an arterial line 90 leading from inlet 92 to the dialysis equipment. Similarly, the equipment is connected to shunt 12 by venous line 94 which delivers purified blood from the dialysis equipment through outlet 96 in the shunt. The direction of blood flow in arterial line 90 is illustrated by arrow 98, and the direction of blood flow in venous line 94 is illustrated by arrow 100.

Although the outlet 96 is downstream from the inlet 92 in shunt 12, nevertheless such a "normal" connection can produce undesired recirculation of purified blood, as illustrated by arrow 102. Thus, purified blood can flow upstream in vein 12 and be picked up at inlet 92 for recirculation through the dialysis equipment, such recirculated blood then making up a part of the arterial blood flow 98.

To measure this recirculation, an indicator material having a selected physical property differing from that of the blood is injected into the venous line 94 through an injection port 104. In the preferred embodiment, the indicator material, indicated by arrow 106, is a saline solution isotonic with the blood, but having different sound velocity properties. The injection of such an indicator dilutes the blood in venous line 94, and if recirculation exists, some of the diluted blood will appear in arterial line 90, producing resultant sound velocity changes which will be recorded by a sensor 110 having a sound source 112 and a sound receiver 114. The receiver 114 is connected by way of line 116 to a detector 118 of the type described in the previous embodiment. The detector serves like as a measuring and evaluating device which records the received signals which calculates the area under the dilution curve which results from the injection of the indicator material, and which carries out the calculations prescribed by the equations described above.

An additional calibration injection of indicator material 120 which is the same as the indicator material 106, may be injected by way of a port 122 in arterial line 90, upstream of the sensor 110. Since all of the blood in the arterial line 90 will pass through the sensor 110, the indicator material injected at 122 will be mixed only with this arterial blood flow, and the resulting dilution curve recorded by detector 118 permits calibration of the system by calculating the area under the dilution curve and subsequent determination of the recirculation fraction in accordance with Equation 10.

If it is desired to avoid the need for a recalibration injection, a modified version of the device of FIG. 6 may be provided, as illustrated in FIG. 7. In this modification, an additional sensor 130 having a sound velocity source 132 and a sound velocity receiver 134 is provided on the venous line 94. The receiver 134 is connected by way of line 136 to the detector 118. The sensor 130 matches sensor 110 and is located downstream of the injection port 104, so that all of the blood from the dialysis equipment 24 as well as the indicator material 106 injected in port 104 will pass through sensor 130. The sensor measures the dilution curve in the arterial blood 100, and the same injection then produces a dilution in the flow 98 through arterial line 90. Sensor 110 detects the indicator material to provide a resulting signal to detector 118 from which the recirculation can be calculated in accordance with Equation 11, as outlined above with respect to the first embodiment and the various modifications thereof described with reference to FIGS. 1-5.

Although the present invention has been described in terms of preferred embodiments, it will be understood that variations and modifications may be made without departing from the true spirit and scope thereof.

We claim:

1. In a method of quantifying a flow rate through a patient blood vessel connected to an external blood circuit having a blood treatment device with a blood withdrawal line and a blood return line, the steps of:
   (a) connecting the blood return line from the blood treatment device to the patient blood vessel upstream of the blood withdrawal line to the blood treatment device;
   (b) establishing a value corresponding to a change in a physical parameter of the blood within the external blood circuit; and
   (c) deriving the flow rate in the patient blood vessel from the established corresponding value.

2. The method of claim 1, further comprising employing a dialyzer as the blood treatment device.

3. The method of claim 1, further comprising inducing the change in the physical parameter of the blood in the blood return line.

4. The method of claim 1, further comprising sensing in the blood withdrawal line the value corresponding to the change in the physical parameter of the blood within the external blood circuit.

5. The method of claim 1, further comprising introducing an indicator into the blood return line.

6. A method of ascertaining a flow rate through a patient arterio-venous shunt connected to a blood treatment device by an arterial line directing blood from the patient arterio-venous shunt to the blood treatment device and a venous line directing blood from the blood treatment device to the patient arterio-venous shunt, the method comprising:
    (a) connecting the arterial line to the patient arterio-venous shunt at a point downstream of a connection of the venous line and the arterio-venous shunt;
    (b) passing a changed blood parameter from the venous line into the patient arterio-venous shunt; and
    (c) ascertaining the flow rate in the patient arterio-venous shunt from a sensed change of the blood parameter in the arterial line.

7. The method of claim 6, further comprising introducing a dilution indicator into the venous line.

8. The method of claim 6, further comprising employing a dialyzer as the blood treatment device.

9. A method of ascertaining a blood flow rate through a shunt connected to an external blood treatment system by an arterial blood line and a venous blood line, the method comprising:
    (a) connecting the arterial blood line to the shunt downstream of a connection of the venous blood line to the shunt;
    (b) operating the external blood treatment system; and
    (c) ascertaining by indicator dilution the blood flow rate through the shunt.

10. The method of claim 9, further comprising measuring an indicator dilution parameter in the arterial blood line.

11. The method of claim 9, further comprising passing an indicator from the venous line into the shunt.

12. A method comprising:
    (a) measuring by indicator dilution a shunt blood flow rate in a patient arterio-venous shunt having an inlet of an arterial line carrying blood from the patient arterio-venous shunt to the dialysis equipment, downstream from an outlet of a venous line returning blood from the dialysis equipment to the patient arterio-venous shunt.

13. A method to facilitate a measurement of a blood flow rate in an arterio-venous shunt, the method comprising the step of:
    (a) calculating by indicator dilution the blood flow rate in the arterio-venous shunt after connecting a first blood line which removes blood from the arterio-venous shunt for delivery to blood treatment equipment, downstream from a second blood line which returns blood from the blood treatment equipment for delivery to the arterio-venous shunt.

14. A method to quantify a blood flow rate in an arterio-venous shunt, the method comprising the step of:
    (a) quantifying by indicator dilution the blood flow rate in the arterio-venous shunt operably connected to dialysis equipment by (i) a venous line returning blood to the arterio-venous shunt from the dialysis equipment and (ii) a downstream arterial line drawing blood from the arterio-venous shunt and delivering the blood to the dialysis equipment.

15. A method for configuring arterial blood line and venous blood line connections between dialysis equipment and an arterio-venous shunt for determining an arterio-venous shunt flow rate, the method comprising:
    (a) changing arterial blood line and venous blood line connections to the arterio-venous shunt from a normal configuration where the arterial line is connected to the arterio-venous shunt upstream from the venous line to a reversed configuration where the arterial line is connected to the arterio-venous shunt downstream from the venous line; and
    (b) determining by indicator dilution the arterio-venous shunt flow rate.

16. A method to facilitate a measurement of a blood flow rate in an arterio-venous shunt, the method comprising the step of calculating the blood flow rate in the arterio-venous shunt after connecting a first blood line which removes blood from the arterio-venous shunt for delivery to blood treatment equipment, downstream from a second blood line which returns blood from the blood treatment equipment, for delivery to the arterio-venous shunt, wherein calculating the blood flow rate in the arterio-venous shunt uses at least one of the following indicator dilution equations or an indicator dilution equation that can be derived from at least one of the following equations:

$$Q=V/S;$$

$$Q_{shunt}=V_{ven}/S_{art}-Q_{dial};$$

$$Q_{shunt}=Q_{dial}(V_{ven}/V_{cal} \times S_{cal}/S_{art}-1);$$

$$Q_{shunt}=(V_{ven}/S_{art}-V_{cal}/S_{cal})$$

$$Q_{shunt}=Q_{dial}(S_{ven}/S_{art}-1):$$

where Q is a rate of blood flow;
V is an amount of indicator;
S is an amount of change in a parameter observed in response to the introduction of an indicator;
$Q_{shunt}$ is a flow rate of blood flowing through the arterio-venous shunt;
$V_{ven}$ is an amount of indicator introduced into the arterio-venous shunt;
$S_{art}$ is an amount of change in a blood parameter observed in an arterial line in response to the introduction of an indicator;
$Q_{dial}$ is a flow rate of blood flowing through a dialyzer in the circulating system;
$V_{cal}$ is a known amount of indicator;
$S_{cal}$ is an amount of change in a blood parameter observed in response to the introduction of $V_{cal}$; and
$S_{ven}$ is an amount of change in a blood parameter observed in a venous line in response to the introduction of an indicator.

17. A method comprising:
    (a) calculating a blood flow rate in an arterio-venous shunt in response to an indicator delivered into the arterio-venous shunt by a hemodialysis treatment venous line, the hemodialysis treatment venous line connected to the arterio-venous shunt upstream from a dialysis equipment arterial line carrying blood from the arterio-venous shunt to the dialysis equipment.

18. The method of claim 17, further comprising introducing the indictor into the venous line.

19. The method of claim 17, further comprising detecting passage of the indicator in the arterial line.

20. The method of claim 17, further comprising calculating the blood flow rate in the arterio-venous shunt using at least one of the following indicator dilution equations or an indicator dilution equation that can be derived from at least one of the following equations:

$$Q = V/S;$$

$$Q_{shunt} = V_{ven}/S_{art} - Q_{dial};$$

$$Q_{shunt} = Q_{dial}(V_{ven}/V_{cal} \times S_{cal}/S_{art}1);$$

$$Q_{shunt} = (V_{ven}/S_{art} - V_{cal}/S_{cal})$$

$$Q_{shunt} = Q_{dial}(S_{ven}/S_{art} - 1):$$

where Q is a rate of blood flow;
V is an amount of indicator;
S is an amount of change in a parameter observed in response to the introduction of an indicator;
$Q_{shunt}$ is a flow rate of blood flowing through the arterio-venous shunt;
$V_{ven}$ is an amount of indicator introduced into the arterio-venous shunt;
$S_{art}$ is an amount of change in a blood parameter observed in an arterial line in response to the introduction of an indicator;
$Q_{dial}$ is a flow rate of blood flowing through a dialyzer in the circulating system;
$V_{cal}$ is a known amount of indicator;
$S_{cal}$ is an amount of change in a blood parameter observed in response to the introduction of $V_{cal}$; and
$S_{ven}$ is an amount of change in a blood parameter observed in a venous line in response to the introduction of an indicator.

* * * * *